US010039626B2

(12) United States Patent
Chu

(10) Patent No.: US 10,039,626 B2
(45) Date of Patent: Aug. 7, 2018

(54) INCONTINENCE SLING, DELIVERY DEVICE AND METHOD OF USE

(71) Applicant: Boston Scientific Scimed, Inc., Maple Grove, MN (US)

(72) Inventor: Michael S.H. Chu, Brookline, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 663 days.

(21) Appl. No.: 14/199,635

(22) Filed: Mar. 6, 2014

(65) Prior Publication Data
US 2014/0257025 A1    Sep. 11, 2014

Related U.S. Application Data

(60) Provisional application No. 61/776,409, filed on Mar. 11, 2013.

(51) Int. Cl.
A61F 2/00       (2006.01)
A61B 17/06      (2006.01)
A61B 17/00      (2006.01)

(52) U.S. Cl.
CPC ...... *A61F 2/0045* (2013.01); *A61B 17/06109* (2013.01); *A61B 2017/00805* (2013.01)

(58) Field of Classification Search
CPC ........ A61B 17/06066; A61B 17/06109; A61B 17/06004; A61B 17/3468;
(Continued)

(56) References Cited

U.S. PATENT DOCUMENTS 4,666,438 A * 5/1987 Raulerson ............. A61M 5/158
                                                 604/166.01
4,874,375 A * 10/1989 Ellison ............... A61B 17/0218
                                                     600/204
(Continued)

FOREIGN PATENT DOCUMENTS

JP      2004526483       9/2004
JP      2005505313 A     2/2005
(Continued)

OTHER PUBLICATIONS

International Preliminary Report on Patentability for PCT Application No. PCT/US2014/021981, dated Sep. 24, 2015, 10 pages.
(Continued)

*Primary Examiner* — Samuel Gilbert
(74) *Attorney, Agent, or Firm* — Brake Hughes Bellermann LLP

(57) ABSTRACT

The present invention discloses a medical assembly and method for the delivery of an implant inside a patient's body. The medical assembly includes a sling assembly including a dilator and an implant. The dilator can be configured to be coupled to the implant. The dilator includes a proximal portion and a distal portion such that the proximal portion includes a first locking feature. The medical assembly includes a delivery device configured to deliver the sling assembly. The delivery device includes a needle and a handle having a proximal portion and a distal portion. The distal portion of the handle includes a second locking feature configured to releasably mate with the first locking feature and inhibit axial movement of the dilator with respect to the delivery device. The first locking feature is sized to frictionally retain the second locking feature.

12 Claims, 17 Drawing Sheets

(58) Field of Classification Search
CPC .......... A61B 2017/00805; A61B 2017/06009; A61B 2017/06076; A61B 2017/0046; A61F 2/0045
USPC .............................................. 600/37, 29–31
See application file for complete search history.

(56) References Cited

U.S. PATENT DOCUMENTS

| | | | | |
|---|---|---|---|---|
| 6,936,052 | B2* | 8/2005 | Gellman | A61B 17/00234 600/29 |
| 7,338,432 | B2* | 3/2008 | Valtchev | A61B 17/06066 600/30 |
| 9,078,730 | B2* | 7/2015 | Smith | A61F 2/0045 |
| 2002/0091373 | A1* | 7/2002 | Berger | A61B 17/0482 606/1 |
| 2002/0099259 | A1 | 7/2002 | Anderson et al. | |
| 2005/0131393 | A1 | 6/2005 | Chu et al. | |
| 2005/0256366 | A1* | 11/2005 | Chu | A61B 17/06066 600/30 |
| 2005/0277807 | A1 | 12/2005 | MacLean et al. | |

FOREIGN PATENT DOCUMENTS

| | | |
|---|---|---|
| JP | 2006517115 A | 7/2006 |
| JP | 2007536004 A | 12/2007 |
| JP | 2010535082 A | 11/2010 |
| WO | 2002071953 | 9/2002 |
| WO | 2006108045 A2 | 10/2006 |
| WO | 2009018372 A2 | 2/2009 |
| WO | 2012119145 A1 | 9/2012 |
| WO | 2014164339 A1 | 10/2014 |

OTHER PUBLICATIONS

International Search Report and Written Opinion for PCT Application No. PCT/US2014/021981, dated Sep. 23, 2014, 16 Pages.
Invitation to Pay Additional Fees and Partial Search Report for PCT Application No. PCT/US2014/021981, dated Jun. 23, 2014, 6 Pages.
First Office Action for Chinese Application No. 201480014477.3, dated Nov. 30, 2016, 17 pages.
Office Action for Japanese Application No. 2016-500889, dated Aug. 22, 2016, 4 pages.

* cited by examiner

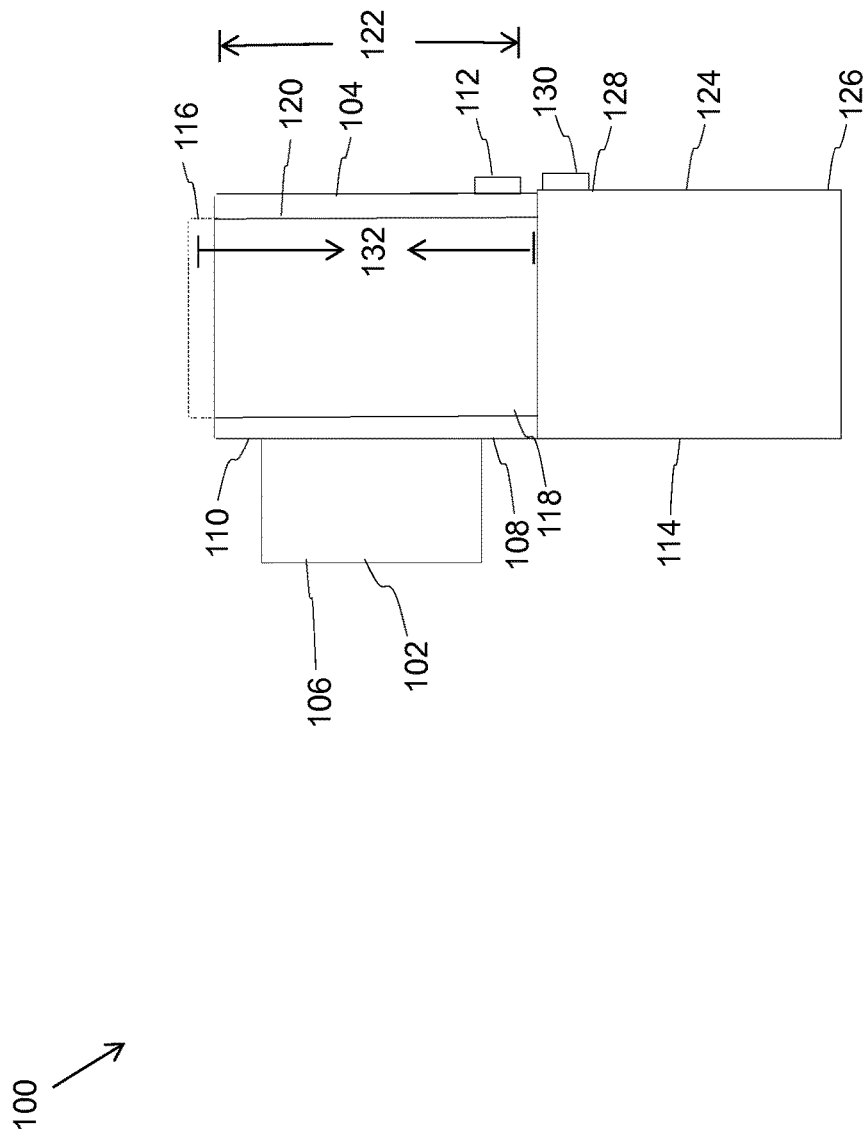

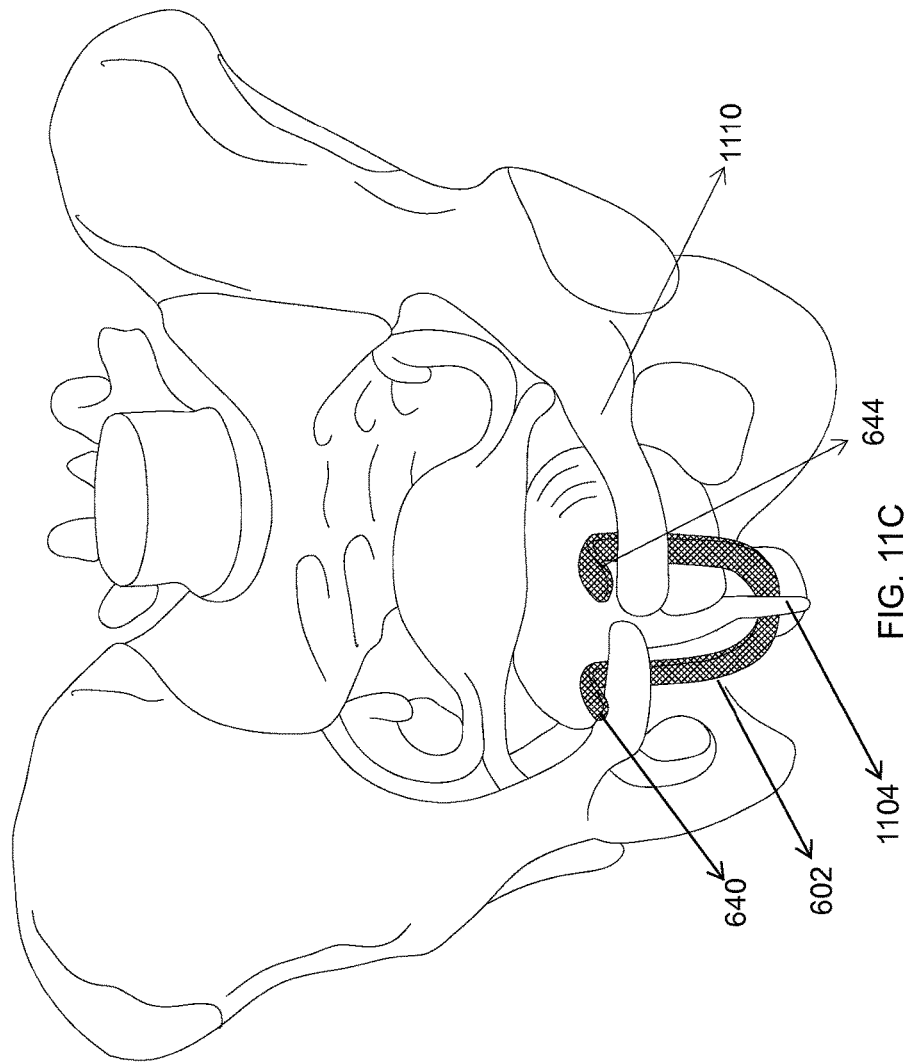

ID-CONTINENCE SLING, DELIVERY
DEVICE AND METHOD OF USE

CROSS-REFERENCE TO RELATED
APPLICATION

This application is a Nonprovisional of, and claims priority to, U.S. Patent Application No. 61/776,409, filed on Mar. 11, 2013, entitled "INCONTINENCE SLING, DELIVERY DEVICE AND METHOD OF USE", which is incorporated by reference herein in its entirety.

BACKGROUND

Field

The present invention generally relates to surgical devices and procedures, particularly devices and methods for the delivery of implants within a patient's body.

Description of the Related Art

Anatomical tissues such as pelvic tissues may be weakened or damaged with age, injury, or disease. This decrease in structural integrity of anatomical tissues may have significant medical consequences, which in turn might influence the biological functions of the tissues. There are various surgical procedures for treating such dysfunction of the tissues. The implants can be placed into a patient to provide support for the weakened or damaged tissue. The support provided by the implant replicates the natural position and structure of the tissue, and thereby helps in decreasing or eliminating impairment of biological functions resulting from tissue weakening or damage.

These surgical methods may use a delivery device to deliver the implant at the anatomical tissue inside the patient's body. Such a delivery device assists in the delivery and placement of the implant. The delivery device may include a needle coupled directly with the implant or through a dilator. The dilator passes through tissues that have already been pierced by the needle, thereby dilating a needle track for ease of the implant introduction and positioning within the patient. A curved and small diameter needle may be used to minimize injury to the patient. Such a long and curved needle may have a tendency to deflect easily and can be difficult to be controlled or directed. A surgeon or operator may need to use his hands to guide the trajectory of a needle tip and prevent the needle from misdirecting and causing injury to the bladder, urethra, bowel or other tissues. Controlling the needle may be even more difficult when the dilator is coupled to the needle. While directing the needle tip, the dilator may tend to advance forward, extending beyond the needle tip, thereby causing difficulties in the advancement of the delivery device.

In view of the above, there is a need for a delivery device and a surgical procedure that facilitates in keeping the dilator intact with the needle, thereby preventing deflection or movement of the needle with respect to the dilator during the surgical procedure. In some embodiments, the device provides the operator with the ability to control the needle trajectory.

SUMMARY

In an embodiment, the present invention discloses a medical assembly and method for the delivery of an implant inside a patient's body. The medical assembly can be configured for treatment of a pelvic floor disorder. The medical assembly includes a sling assembly, including a dilator and an implant. The dilator can be configured to be coupled to the implant. The dilator includes a proximal portion and a distal portion such that the proximal portion includes a first locking feature. The medical assembly includes a delivery device configured to deliver the sling assembly. The delivery device includes a needle having a proximal portion and a distal portion such that the dilator is positioned over the needle. The delivery device further includes a handle having a proximal portion and a distal portion such that the distal portion of the handle is coupled to the proximal portion of the needle. The distal portion of the handle includes a second locking feature configured to releasably mate with the first locking feature and inhibit axial movement of the dilator with respect to the delivery device. The first locking feature sized to frictionally retain the second locking feature.

In an embodiment, the present invention discloses a medical assembly configured for treatment of a pelvic floor disorder. The medical assembly includes an implant for placement in a body of a patient. The medical assembly includes a dilator configured to be coupled to the implant. The dilator includes a proximal portion and a distal portion such that the proximal portion includes an aperture. The medical assembly further includes a delivery device configured to deliver the implant. The delivery device includes a hollow needle having a proximal portion and a distal portion such that the dilator is positioned over the hollow needle. The delivery device further includes a handle having a proximal portion and a distal portion such that the distal portion of the handle is coupled to the proximal portion of the needle. The distal portion of the handle includes a protrusion configured to releasably fit into the aperture and inhibit axial movement of the dilator with respect to the delivery device. The aperture is sized to frictionally retain the protrusion of the delivery device. The delivery device can include an injector configured to be coupled to the proximal end portion of the handle allowing passage of a fluid through the hollow needle.

In yet another embodiment, the present invention discloses a method for treatment of a pelvic floor disorder in a patient's body. The method includes inserting a delivery device along with a dilator inside the patient's body. The dilator includes an aperture at its proximal end portion. The delivery device further includes a handle such that the handle includes a protrusion at its distal end portion such that the protrusion is sized to fit in the aperture, thereby preventing an axial movement of the dilator with respect to the delivery device. The method further includes disassociating the dilator from the delivery device once the delivery device reaches a target body location in a pelvic floor region by moving the dilator against the protrusion. The dissociation allows the protrusion to exit the aperture. The method includes implanting a bodily implant at a first portion within the pelvic floor region.

BRIEF DESCRIPTION OF THE FIGURES

The invention and the following detailed description of certain embodiments thereof may be understood with reference to the following figures:

FIG. 1 is a schematic diagram of a medical assembly, in accordance with an embodiment of the present invention.

FIG. 11C illustrates implantation of a portion of the medical assembly inside a female body through a retropubic approach.

DETAILED DESCRIPTION

Figure 2A:
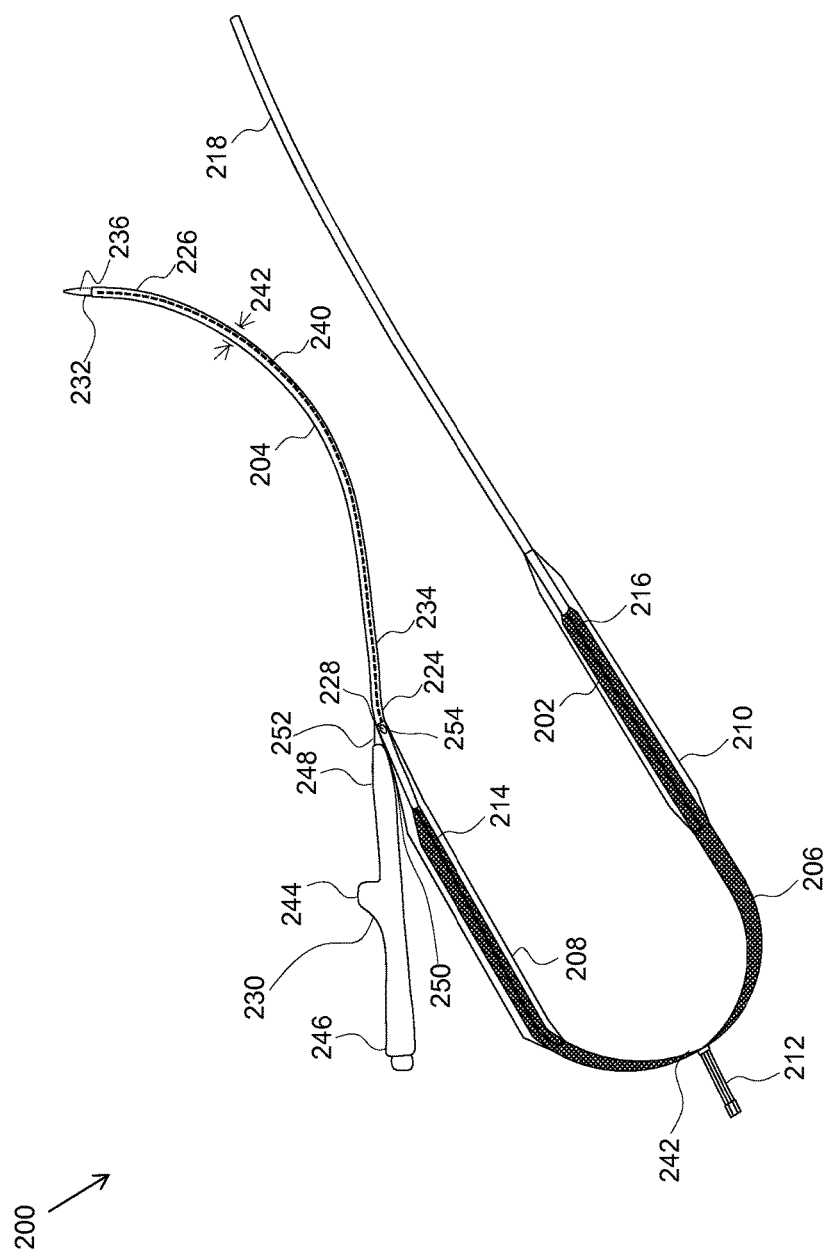
FIG. 2A is a perspective view of a medical assembly, in accordance with an embodiment of the present invention.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The terms proximal and distal described in relation to various medical devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like, who may perform the procedure of surgery through the patient's body orifice as described in the present invention. The term proximal refers to an area that is closest to the operator. The term distal refers to an area that is farthest from the operator. The patient referred here can be a human female, male or any other mammal.

FIG. 1 is a schematic diagram of a medical assembly 100 configured to treat a pelvic floor disorder. The medical assembly 100 includes a sling assembly 102. The sling assembly 102 can be, for example, a retropubic incontinence sling configured to be delivered by way of a transvaginal approach or a transobturator approach or vaginal pre-pubic approach or can be delivered through other approaches and positioned at various locations within a patient's body. In an embodiment, the sling assembly 102 can include a dilator 104 and an implant 106.

The dilator 104 can include a proximal portion 108 and a distal portion 110. The dilator 104 can be configured to be coupled to the implant 106. The dilator 104 can be configured to expand an opening in a patient's body allowing insertion of the implant 106 and a delivery device as they follow the dilator 104 into the opening within a patient's body. In an embodiment, the dilator 104 can be made from one or more biocompatible materials such as a plastic or metal. In an example, the dilator 104 can be made of a semi-rigid plastic material. Examples of such materials include, but are not limited to, polyethylene terephthalate (PET), polyethylene (PE), or ethylene vinyl acetate (EVA). In some embodiments, the cross section of the dilator 104 can be circular, substantially flat or triangular in shape or can be of any other shape. In other embodiments, the cross section of the dilator 104 can be substantially rectangular and tapered at the distal portion 110. In embodiments, the dilator 104 can be employed of any shape as per the requirements in a specific surgical procedure. In an embodiment, the dilator 104 is a first dilator that can be attached to a first end portion of the implant 106. In an embodiment, a second dilator that can be similar to the dilator 104 can be attached to a second end portion of the implant 106.

The proximal portion 108 of the dilator 104 includes a first locking feature 112. In an embodiment, the first locking feature is an aperture 112. The aperture 112 can be formed of various shapes and sizes. Exemplary shapes can be a rectangle, a square, or an oval shape. In certain embodiments, the aperture 112 can assume a circular shape.

The medical assembly 100 includes a delivery device 114 such that the delivery device 114 can be configured to deliver the sling assembly 102 to a target location inside the body. The delivery device 114 can include a needle 116. The diameter and length and curvature of the needle 116 can depend based on the surgical requirements. In certain embodiments, the delivery device 114 can be designed so as to be adapted to be used in the trans-vaginal retro pubic approach. In certain embodiments, the needle 116 can be a surgical needle 116 with a substantially small outer diameter for minimally invasive surgery.

The needle 116 has a proximal portion 118 and a distal portion 120. The needle 116 may include a tip portion at its distal portion 120. In some embodiments, the tip portion may be sharp and configured to dissect tissue layers and create a passageway within bodily tissues to deliver and place the implant 106 inside the patient's body. In some embodiments, the needle 116 can be made of stainless steel or other medical grade metal.

According to various embodiments of the present invention, the dilator 104 can be configured to be coupled to the needle 116. In an embodiment, the dilator 104 can be positioned over the needle 116 by sliding the dilator 104 over the needle 116, thereby forming a removable connection between the two. In an embodiment, the dilator 104 can include a hollow passageway along a length 122 of the dilator 104 extending between the distal portion 110 to the proximal portion 108 of the dilator 104. In some embodiments, the dilator may include grooves on the surface instead of, or in addition to, the lumen. In some embodiments, the grooves may be configured to conduct fluids along the outside of the dilator. The hollow passageway allows the needle 116 to be inserted within the dilator 104. Owing to the flexible nature of the dilator material, the dilator 104 can be sized to assume the shape of the needle 116 on its insertion. In an embodiment, the length 122 of the dilator 104 can be longer than a length 132 of the needle 116 such that the dilator 104 slides over the needle 116 and the proximal portion 108 of the dilator 104 extends beyond the proximal portion 118 of the needle 116 in a manner that the proximal portion 108 of the dilator couples with a portion of the sling assembly 102. In an embodiment, the proximal portion 108 of the dilator 104 can be extended distally to overlap with or partially enclose the sling assembly 102 including the implant 106.

The delivery device 114 further includes a handle 124. In some embodiments, the handle is made up of a plastic material. Exemplary plastic materials include polycarbonate, lexan, Acrylonitrile butadiene styrene (ABS), and the like without limitations. In an embodiment, the handle 124 has a proximal portion 126 and a distal portion 128 such that the distal portion 128 of the handle 124 can be coupled to the proximal portion 118 of the needle 116. In an embodiment, the distal portion 128 of the handle 124 can include a second locking feature 130. The second locking feature 130 can be configured to releasably mate with the first locking feature 112. In an embodiment, the second locking feature 130 is a protrusion. In some embodiments, various other kinds of locking features such as gear, push button, hole, slider, and threads can be used to form the first locking feature 228 and the second locking feature 250. In an example, the first locking feature can be a friction lock that is configured to lock the second locking feature 250 by moving the first locking feature 228 with respect to the second locking feature 250. In other embodiments, the first locking feature can be a thread lock having a set of male threads provided on the dilator 204 that are configured to engage female threads of the second locking feature provided on the delivery device and lock the dilator 204 with respect to the delivery device 230. In an embodiment, the first locking feature 112, provided at the proximal portion 108 of the dilator 104, can be sized to frictionally retain the second locking feature 130, provided on the distal portion 128 of the handle 124, thereby allowing a slight frictional engagement between the dilator 104 and the delivery device 114. In an embodiment, the first locking feature is configured to frictionally retain the second locking feature at one location. The frictional engagement can serve to form a seal or a coupling between the dilator 104 and the handle 124, thereby inhibiting axial movement of the dilator 104 with respect to the delivery device 114. In various embodiments, the first locking feature 112 can be the protrusion whereas the second locking feature 130 can be the aperture or vice versa. In an embodiment, multiple locking features similar to the first locking feature 112 and the second locking feature 130 can be provided in the medical assembly 100. In accordance with several other embodiments, various other types of engagement mechanism can be employed such as but not limited to snap fitting, thread fitting, bolt jointing, riveting, and the like.

In an embodiment, the medical assembly 100 can include an injector configured to be coupled to the proximal portion 126 of the handle 124 and configured to deliver a fluid through the passageway to a location inside the body. The injector can deliver medication such as anesthetics, medications, other fluids to assist in the healing process, or any other fluids at a target location inside the patient's body. The injector can be or include a fluid pump, nozzle, plunger, valve, syringe or similar devices that are configured to draw the fluid in by such as converting pressure energy into velocity.

FIG. 2A is a perspective view of a medical assembly 200 for the treatment of a pelvic floor disorder, in accordance with an embodiment of the present invention. The medical assembly 200 includes a sling assembly 202. The sling assembly 202 can be a retropubic incontinence sling configured to be delivered by way of a transvaginal approach or a transobturator approach or vaginal pre-pubic approach. In accordance with various embodiments, various sling assembly configurations can be possible. An exemplary sling assembly configuration, as shown in FIG. 2A, can be configured to include a first dilator 204, an implant 206, a first sleeve 208, and a tab 212. In an example, the implant 206 of the sling assembly 202 can be comprised of a polypropylene knitted mesh protected by disposable plastic sleeve such as the first sleeve 208. At a first end portion 214 of the implant 206 is attached the first dilator 204. The first dilator 204 can be configured to facilitate passage of the implant 206 or a delivery device used to carry the implant 206 through bodily tissues for the transvaginal placement or through any other approach of placement. In another embodiment, a middle portion 242 of the implant 206 can be marked by the tab 212. In an embodiment, the first dilator 204 can be coupled to the implant 206 through a suture. In an exemplary embodiment, the suture can form a first association loop to couple the first dilator 204 with the implant 206. Various other coupling mechanisms or modes selected at least from the group consisting of glue, a staple, a fastener, or thread can be used to couple the dilator 204 with the implant 206. In other embodiments, the implant 206 may be coupled to the sleeve 208 and the first sleeve 208 may be coupled to the first dilator 204. Sleeve 208 may extend along a partial length or a full length of implant 206. More than one sleeve 208 may be utilized, for ex ample, a sleeve on each half of the implant relative to tab 212. In an embodiment, the first sleeve 208 is wrapped around and attached to at least a portion of the dilator 204. In an embodiment, the first dilator 204 can include a proximal portion 224 and a distal portion 226. The proximal portion 224 of the first dilator 204 can include a first locking feature 228. The first locking feature can be an aperture 228.

In accordance with various embodiments of the present invention, the medical assembly 200 can include a delivery device 230 configured to deliver the sling assembly 202. In an embodiment, the delivery device 230 can include a needle 232. In an embodiment, the needle 232 can be a surgical needle with a substantially small outer diameter for minimally invasive surgery. The needle 232 has a proximal portion 234 and a distal portion 236. In an embodiment, the first dilator 204 can be positioned along a length of the needle 232. In an embodiment, the first dilator 204 can include a hollow passageway 240 along the length of the first dilator 204 extending between the distal portion 226 and the proximal portion 224 of the first dilator 204. The hollow passageway allows the needle 232 to be inserted within the first dilator 204. In some embodiments, the first dilator 204 may include a groove or grooves along a surface of the first dilator 204. In some embodiments, the first dilator 204 can be made of resilient or flexible material such that upon insertion of the needle 232, the first dilator 204 can be configured to be stretched due to its flexible material, thereby increasing a width 242 of the passageway to an extent that makes the receipt of the needle 232 possible within the passageway 240. In some other embodiments, the passageway 240 of the first dilator 204 can be sized to fit into the needle 232 upon insertion of the needle 232 within the first dilator 204. In an embodiment, the first dilator 204 is open ended and tapered at one of its end to allow the needle 232 to protrude.

In an embodiment, the first dilator 204 can be positioned over the needle 232 in a manner that the distal portion 226 of the first dilator 204 is located near the distal portion 236 of the needle 232. In another embodiment, the proximal portion 224 of the first dilator 204 extends beyond the proximal portion 234 of the needle 232 in a manner that the proximal portion 224 of the first dilator 204 can be coupled to the first sleeve 208 of the implant 202 through the suture. In an embodiment, a second dilator 218, similar to the first dilator 204, can be configured to be coupled at a second end portion 216 of the implant 206. In an embodiment, the second end portion 216 of the implant 206 can be protected by a second sleeve 210. The second dilator 218 can be positioned along a length of a needle similar to the needle 232 described above.

Figure 2B:
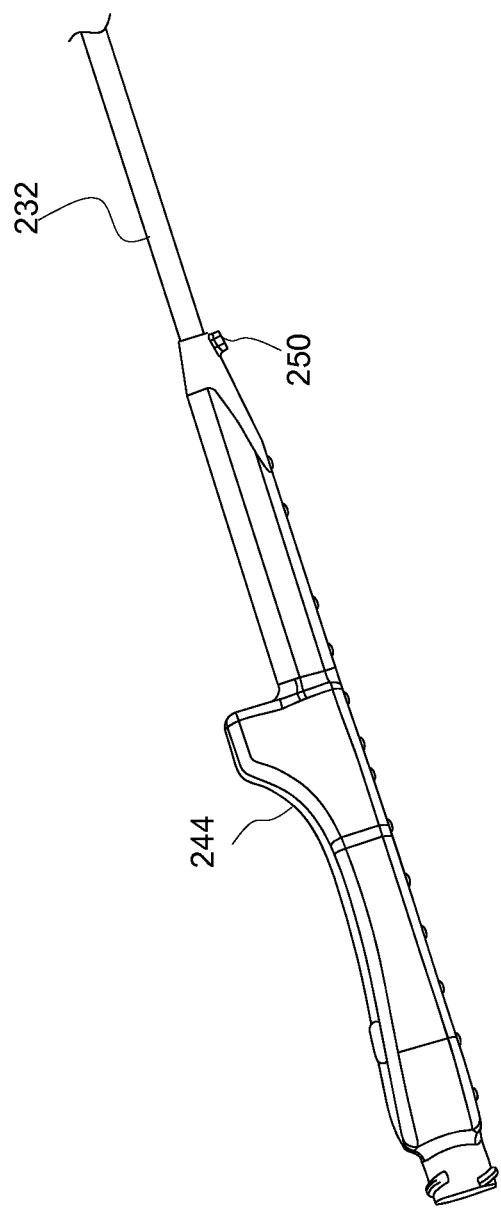
FIG. 2B is a perspective view of a portion of the medical assembly of FIG. 2A, in accordance with an embodiment of the present invention.

The delivery device 230 further includes a handle 244 having a proximal portion 246 and a distal portion 248 and the needle 232 extends from the distal portion 248 of the handle 244. In an embodiment, the distal portion 248 of the handle 244 can include a second locking feature 250. The second locking feature 250 can be configured to releasably mate with the first locking feature 228. In an embodiment, the second locking feature 250 is a protrusion, as shown in FIG. 2B. FIG. 2B illustrates a portion of the medical assembly 200 of FIG. 2A with an enlarged view of the second locking feature 250. In accordance with various embodiments of the present invention, the first locking feature 228, provided at the proximal portion 224 of the first dilator 204, can be sized to frictionally retain the second locking feature 250. The second locking feature 250 is provided on the distal portion 248 of the handle 244. In such embodiments, the locking features allow a slight frictional engagement between the first dilator 204 and the delivery device 230. This frictional engagement can serve to form a seal or coupling between the first dilator 204 and the handle 244, thereby inhibiting axial movement of the dilator 204 with respect to the delivery device 230.

In some embodiments, the first dilator 204 can be slid onto the needle 232 of the delivery device 230, thereby allowing coupling of the sling assembly 202 with the delivery device 230.

Figure 2C:
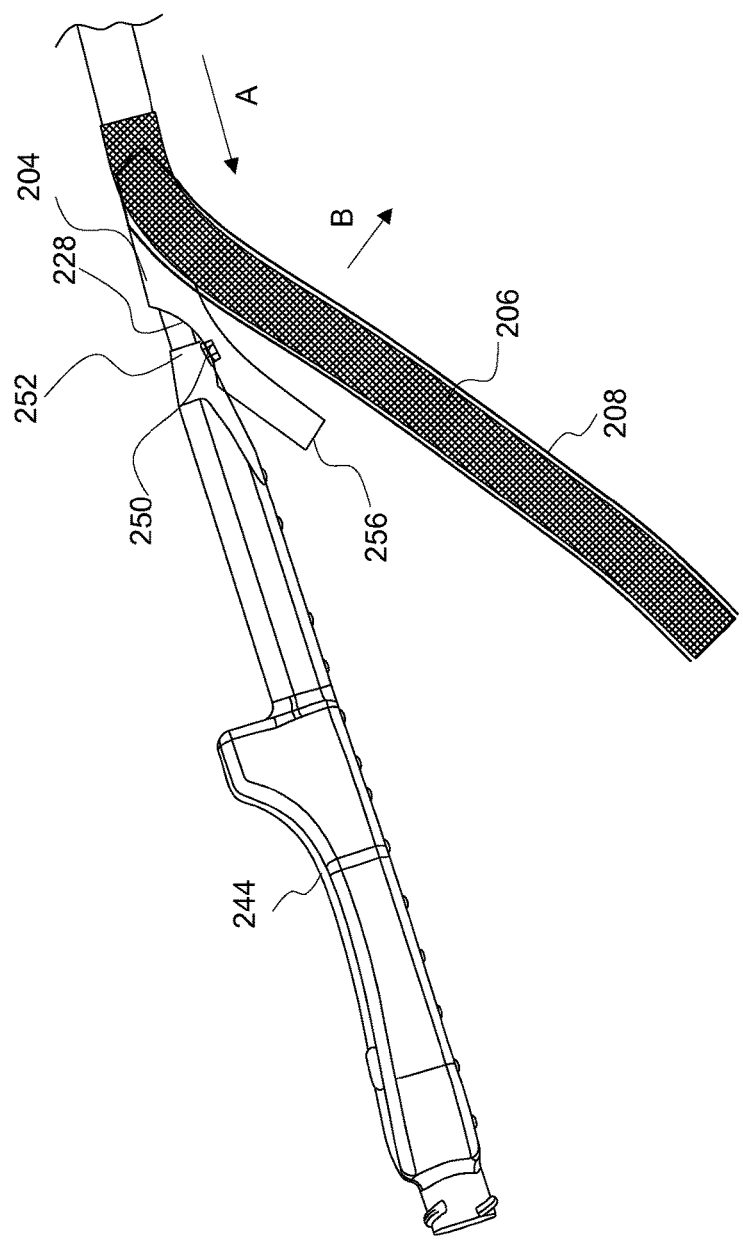
FIG. 2C is another perspective view of the medical assembly of FIG. 2A, in accordance with an embodiment of the present invention.

FIG. 2C, is a perspective view of a portion of the medical assembly 200 of FIG. 2A, in accordance with an embodiment of the present invention. As shown in FIG. 2C, in an embodiment, the proximal portion 224 of the first dilator 204 can include or be coupled to a dilator tab 256. In an embodiment, the dilator tab 256 can be defined by an extended portion or a separately attached portion at the proximal portion 224 of the first dilator 204 that can allow pivoting or bending of the tab 256 with respect to rest of the portion of the first dilator 204. In an embodiment, the proximal portion 224 of the first dilator 204 can be flattened so as to define the extended portion configured as the dilator tab 256. As shown in FIG. 2C, an advancement of the first dilator 204 in a direction of arrow A causes the dilator tab 256 to abut to the protrusion 250 and deflect in the direction of arrow B and the aperture 228 to snap over the protrusion 250 of the handle 244. The alignment of the aperture 228 over the protrusion 250 provides contact between edges of the aperture 228 and a side 254 of the protrusion 250, thereby causing the frictional resistance between the aperture 228 and the protrusion 250. The frictional resistance causes the first dilator 204 to be releasably locked with respect to the delivery device 230. In an embodiment, the frictional resistance prevents the locked first dilator 204 from undesired slipping or releasing in a direction opposite to the direction of arrow A. In an embodiment, a physician or an operator can manually position the aperture 228 over the protrusion 250 by grasping the dilator tab 256 and pulling it in the direction of arrow A and arrow B. In an embodiment, the handle edge 252 and an inside diameter of the first dilator 204 and the aperture 228 prevents the first dilator 204 from advancing in the direction of arrow A. In an embodiment, the dilator tab 256 facilitates in disassociation of the first dilator 204 from the delivery device 230.

Figure 3A:
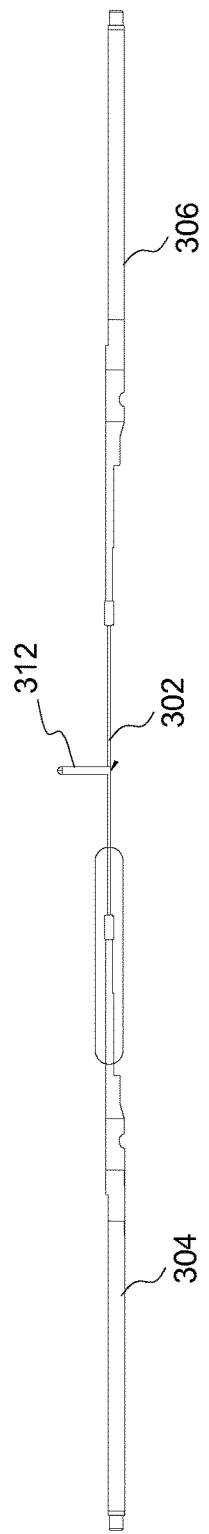
FIGS. 3A-3B illustrate an exemplary sling assembly, in accordance with the embodiments of FIGS. 2A-2C of the present invention.
Figure 3B:
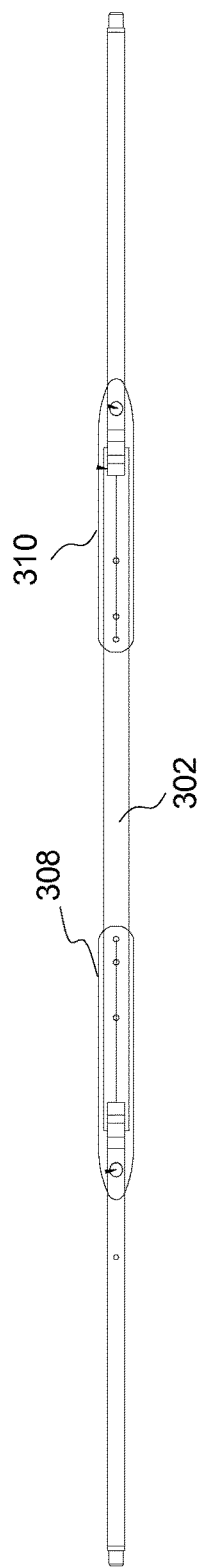
Figure 4:
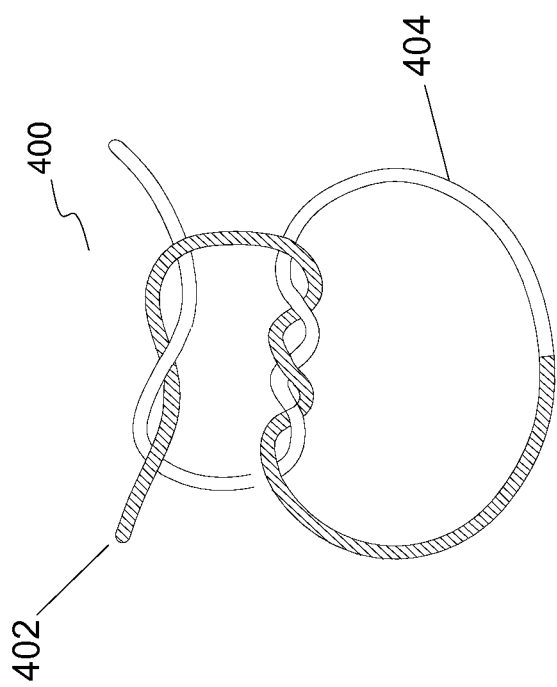
FIG. 4 is a perspective view of a double surgeon's knot or association of a tab with an implant, in accordance with an embodiment of the present invention.

FIGS. 3A-3B illustrate an exemplary sling assembly 300, in accordance with some embodiments of the present invention. In an embodiment, as shown in FIGS. 3A and 3B, the sling assembly 300 includes the implant 302, the first and the second dilator 304 and 306, the first and second sleeve 308 and 310 and the center tab 312. The implant 302 can be a polypropylene mesh. In an embodiment, the tensile strength of the implant 302 is 7.5 pound/minute (LB Min). In an embodiment, the implant 302 has a length of 40 cm wherein, the center tab 312 can be placed at half of the distance of the length of the implant 302. In an embodiment, the center tab 312 to the implant 302 tensile strength can be 7.5 LB Min. In some embodiments, as shown in FIG. 4, a double surgeon knot 400 can be used to associate the center tab 312 to the implant 302. The shaded portion 402 of the suture 406 and the non-shaded portion 404 of the suture 406 are shown for simplicity of illustration and description so as to represent the way the suture 406 is tied to form the knot 400. In an embodiment, a single suture with two ends looped through the implant 302 and tied together can form the knot 400.

In an embodiment, the sleeves 308 and 310 can contain folds. In an embodiment, the center tab 312 is positioned on a surface of the sleeves 308 and 310 opposite the surface that contains folds of the sleeves 308 and 310. The sleeve folds are junctions between the dilators 304 and 306 and the respective sleeves 308 and 310 where the sleeves 308 and 310 are wrapped around the dilators 304 and 306. In an embodiment, the center tab 312 is oriented in a manner that it resides on an opposite side of the sleeves 308 and 310 where apertures of the dilators 304 and 306 reside. In this position, when inserting a needle such as similar to the needle 232 into the dilators 304 and 306, the center tab 312 sits hanging downward from the implant 302.

Figure 5:
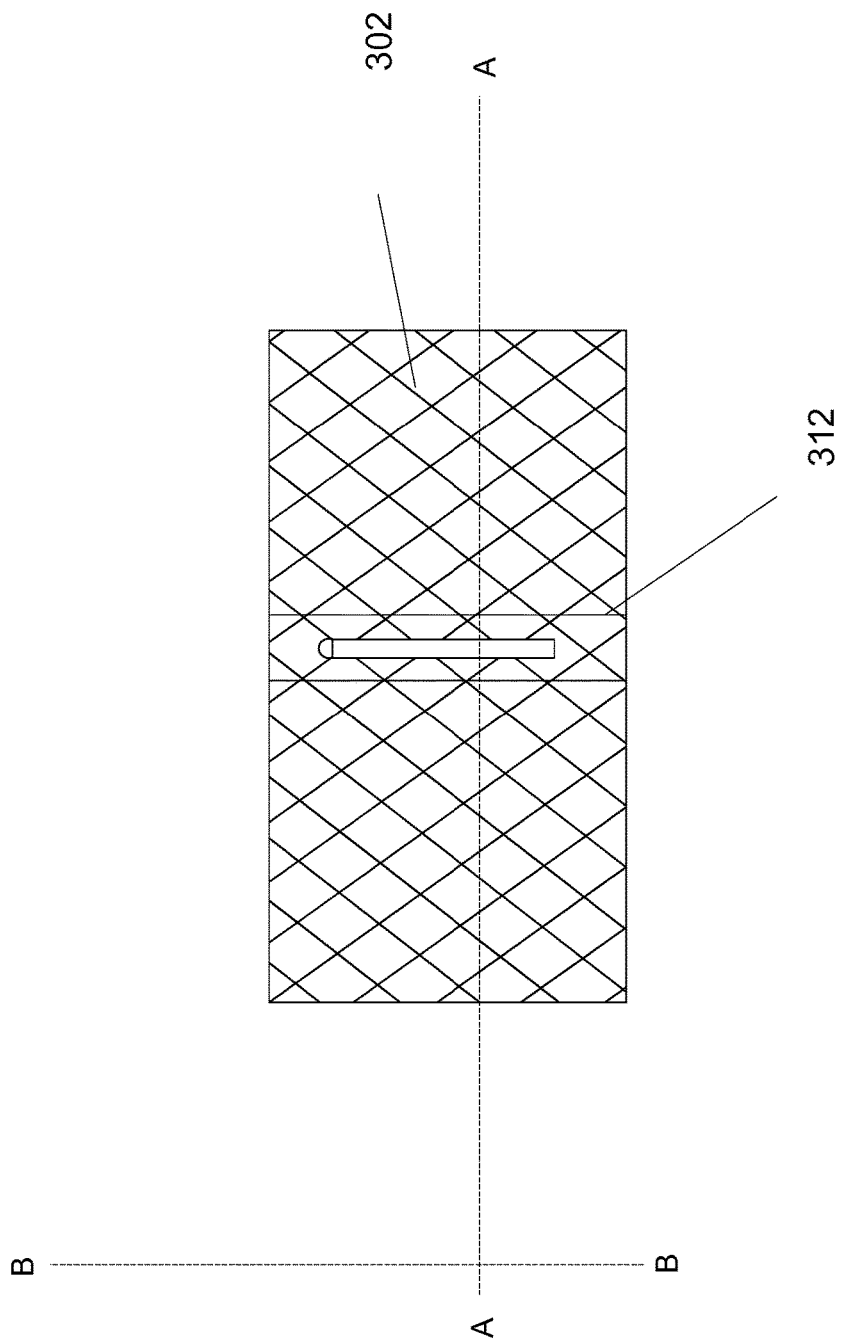
FIG. 5 illustrates a top view of a portion of the implant with a center coupled thereto, in accordance with an embodiment of the present invention.

FIG. 5 shows a top view of a portion of the implant 302 with an exemplary coupling of the center tab 312 with the implant 302. The center tab 312 can be coupled by such as stitches using threads or sutures and the like elements. In various embodiments, stitch pattern for coupling the implant 302 with the center tab 312 can be of various types. For example, in an embodiment, the stitch pattern can be vertically aligned with respect to the implant 302 such that the direction B-B of the stitch pattern is orthogonal with respect to longitudinal axis A-A of the implant 302, as shown in FIG. 5. In another embodiment, the stitch pattern can be horizontally aligned with respect to the implant 302 such that the direction B-B of the stitch pattern is parallel with respect to the longitudinal axis A-A of the implant 302. In an embodiment, one or more stitches can be made for coupling the center tab 312 with the implant 302 by moving the thread in and out of and through the implant 302 once or several times. For example, in an embodiment, the thread can pass through the implant 302 once, or twice, or thrice, or four times, or even more as per the requirements. In an embodiment, a single stitch threaded in and out through the implant 302 can be provided so as to allow easy removal after the loop is cut.

Referring again to FIGS. 3A-3B, in an embodiment, the first sleeve 308 and the second sleeve 310 can be folded at implant's ends. In an embodiment, the mesh movement within the sleeves 308 and 310 is less than or equals 3 millimeter (mm). In an embodiment, the first and the second sleeve 308 and 310 can be coupled to the first and the second dilator 304 and 306 in a manner that the bonding strength of the first sleeve 308 to the first dilator 304 and the second sleeve 310 to the second dilator 306 is 7.5 LB Min. In an embodiment, the gap between the center tab 312 and the implant 302 is less than 0.015 inch. In an embodiment, the center tab 312 may be positioned within a range of 0.0125 inch from the center of the implant 302. In some embodiments, a suture is coupled to or woven through the implant and is coupled to one of the sleeves, such as the first sleeve 308 to couple the first sleeve 308 to the implant.

As per the various embodiments described above, various configurations of the sling assembly 202 and the various kinds of locking features can be possible in the medical assembly 200. In some embodiments, the handle 244 can be configured to include the aperture 228 and the dilator 204 can be configured to include the protrusion 250 such that the protrusion 250 provided on the dilator 204 can snap into the aperture 228 of the handle 244 to secure and lock the dilator 204 with respect to the delivery device 230.

In another embodiment, the protrusion 250 can be provided on the needle 232 and the aperture 228 can be provided onto the dilator 204 such that the aperture 228 provided onto the dilator 204 can be sized to snap into the protrusion 250 of the dilator 204.

In some embodiments, the first locking feature 228 and the second locking feature 250 can be provided at various portions of the medical assembly 200. For example, in some embodiments, the first locking feature 228 such as an opening or an aperture can be provided on the delivery device 230, whereas the second locking feature 250 such as a protrusion can be located on a portion of the sling assembly 202. For example, the second locking feature 250 such as the protrusion can be located on the sleeves of the sling assembly 202.

Figure 6:
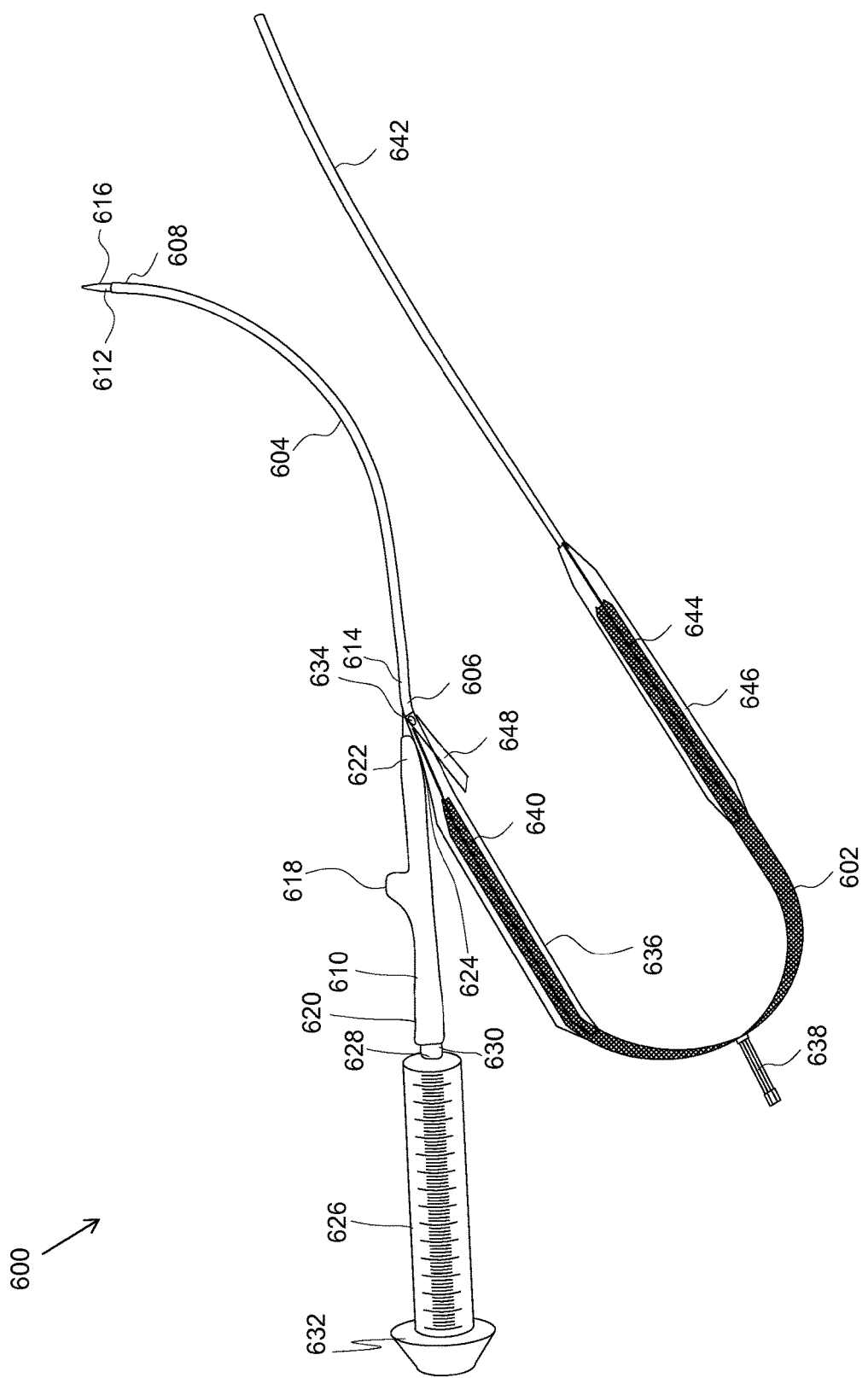
FIG. 6 is a perspective view of a medical assembly including an injector, in accordance with an embodiment of the present invention.

FIG. 6 is a perspective view of the medical assembly 600, in accordance with an embodiment of the invention. The medical assembly 600 can be configured for the treatment of a pelvic floor disorder. The medical assembly 600 includes an implant 602, a first dilator 604, a first sleeve 636, and a tab 638. In an embodiment, the first dilator 604 can be attached at a first end portion 640 of the implant 602. The first dilator 604 includes a proximal portion 606 and a distal portion 608 such that the proximal portion 606 includes an aperture 634. In an embodiment, the proximal portion 224 of the first dilator 204 can include or be coupled to a dilator tab 256. In an embodiment, the dilator tab 256 can be defined by a flattened proximal portion 224 of the first dilator 204. In an embodiment, the dilator tab 256 can be close ended, rounded and defined short in length. In an embodiment, a second dilator 642, similar to the first dilator 604, can be configured to be coupled at a second end portion 644 of the implant 602. In an embodiment, the second end portion 344 of the implant 602 can be protected by a second sleeve 646.

In an embodiment, a delivery device 610 can be configured to deliver the implant 602 within a patient's body. The delivery device 610 can include a hollow needle 612 having a proximal portion 614 and a distal portion 616 such that the first dilator 304 is positioned over the hollow needle 612. In some embodiments, the needle 612 may have or define grooves along an outer surface. In an embodiment, the needle 612 is a surgical needle with a substantially small outer diameter for minimally invasive surgery. The delivery device 610 includes a handle 618 having a proximal portion 620 and a distal portion 622 such that the distal portion 622 of the handle 618 can be coupled to the proximal portion 614 of the needle 612. The distal portion 622 of the handle 618 includes a protrusion 624 configured to releasably fit into the aperture 634 such that the alignment of the aperture 634 over the protrusion 624 inhibits axial movement of the first dilator 604 with respect to the delivery device 610. The aperture 634 can be sized to frictionally retain the protrusion 624 of the delivery device 610. The first dilator 304 can be locked with respect to the delivery device 610 in a manner similar to the locking described with respect to FIGS. 1 and 2A-2C. In an embodiment, the dilator tab 648 can be configured to facilitate in disassociation of the first dilator 604 from the delivery device 610.

The medical assembly 600 includes an injector 626 configured to be coupled to the proximal end portion 620 of the handle 618 allowing passage of a fluid through the hollow needle 612. The injector can be configured to deliver medication such as anesthetics, medications, other fluids to assist in the healing process, or any other fluids to a target tissue in the patient's body. In an embodiment, the medical assembly 600 can include at least one injector port 628 having a through lumen 630 and can be configured to connect the injector 626 with the handle 618. In an embodiment, a single or multiple injector ports 628 can be coupled at the proximal portion 620 of the handle 618. In another embodiment, the injector port 628 can be an integral portion of the delivery device 610. In yet another embodiment, the injector port 628 can be removably coupled to the delivery device 610. In an embodiment, the injector 626 can be a syringe having an associated plunger 632 coupled to the injection port 628. Upon depression of the plunger 632, fluid flows from the syringe 626 through the injection port 628, out through the handle 618, and into the hollow needle 612 and further into the patient's body. In some embodiments, the injection port 628 and the associated syringe 626 can be located at any suitable place along the delivery device 610. In some embodiments, the injection port may be located along the length of the needle and the dilator as well as at the end portion. In some embodiments the syringe is attached to the injection port with a luer lock.

Figure 7:
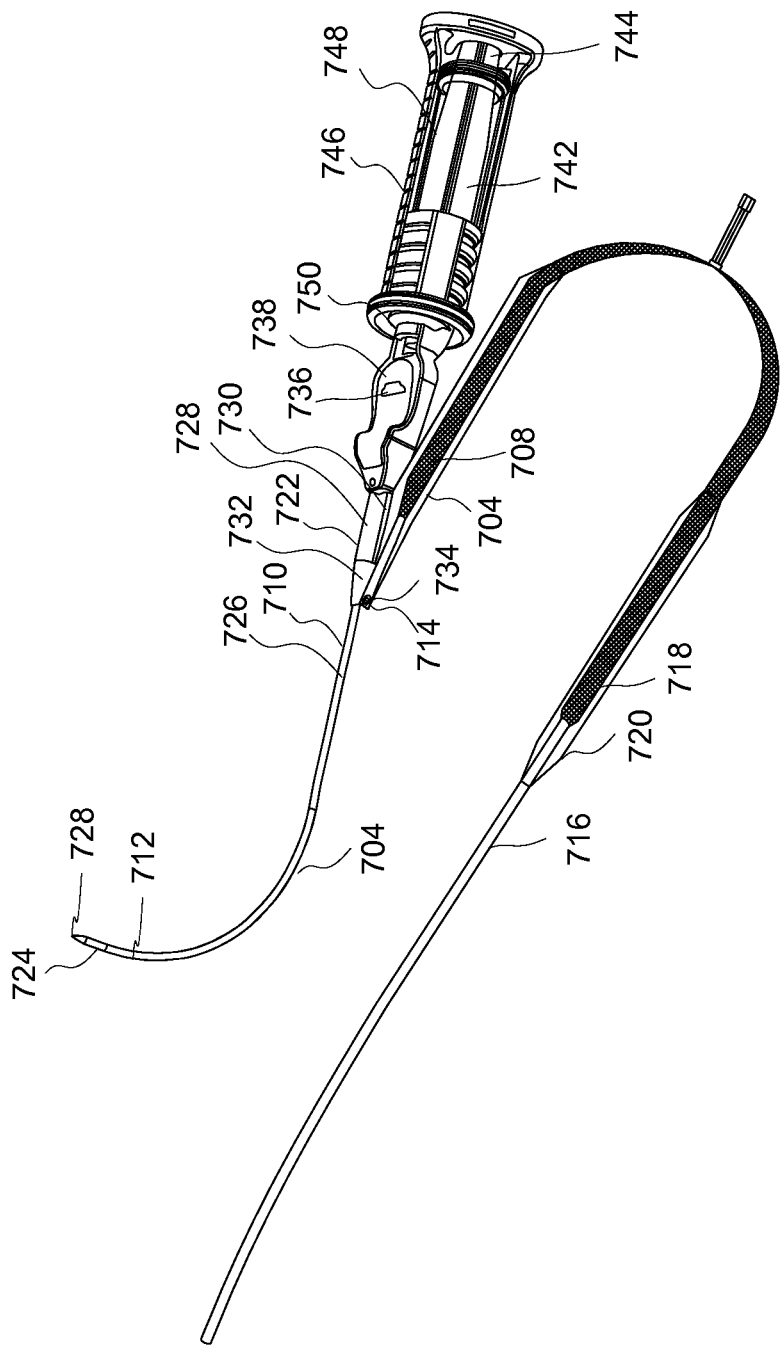
FIG. 7 is a perspective view of a medical assembly, in accordance with an embodiment of the invention.

FIG. 7 is a perspective view of a medical assembly 700, in accordance with an embodiment of the invention. The medical assembly 700 includes an implant 702, a first dilator 704, a first sleeve, and a tab 706. In an embodiment, the first dilator 704 can be attached at a first end portion 708 of the implant 702. The first dilator 704 includes a proximal portion 710 and a distal portion 712 such that the proximal portion 710 includes an aperture 714. In an embodiment, a second dilator 716, similar to the first dilator 704, can be coupled at a second end portion 718 of the implant 702. In an embodiment, the second end portion 718 of the implant 702 can be protected by a second sleeve 720.

In an embodiment, a delivery device 722 can be configured to deliver the implant 702 within a patient's body. The delivery device 722 can include a hollow needle 724 having a proximal portion 726 and a distal portion 732 such that the first dilator 702 is positioned over the hollow needle 724. The delivery device 722 includes a handle 728 having a proximal portion 730 and a distal portion 732 such that the distal portion 732 of the handle 728 can be coupled to the proximal portion 726 of the needle 724. The distal portion 732 of the handle 728 includes a protrusion 734 configured to releasably fit into the aperture 714 to frictionally retain the protrusion 734 of the delivery device 722. The first dilator 704 can be locked with respect to the delivery device 722 in a manner similar to the locking described with respect to FIGS. 1, 2A-2C and 6.

In an embodiment, the proximal portion 726 of the handle 728 includes a luer hub 736 and a luer support 738. The luer hub 736 is configured to interconnect the delivery device 722 with an injector assembly 740.

The injector assembly 740 is configured to be coupled to the proximal end portion 730 of the handle 728 and allowing passage of a fluid through the hollow needle 724. The injector assembly 740 can be configured to deliver medication such as anesthetics, medications, other fluids to assist in the healing process, or any other fluids to a target tissue in the patient's body. In an embodiment, the injector assembly 740 includes a syringe 742, an associated plunger 744 and an injector adapter 746. The plunger 744 can be pulled and pushed along inside a barrel 748 of the syringe 742, allowing the syringe 742 to take in and expel a liquid or gas through an orifice 750 at the open end of the barrel 748. The injector adaptor 746 is configured to hold the syringe 742.

In an embodiment, the luer hub 736 and the luer support 738 prevent the luer from snap off when a force is asserted on the syringe 742 when used as the handle 728.

Figure 8:
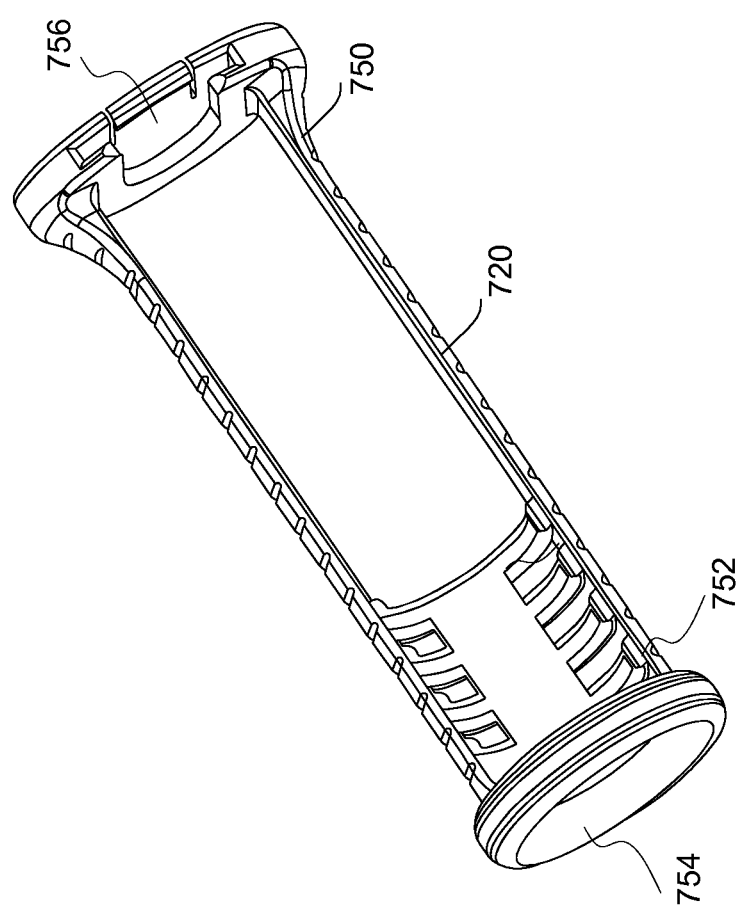
FIG. 8 is an enlarged and isolated perspective view of an injector adaptor of the medical assembly of FIG. 7, in accordance with an embodiment of the present invention.

FIG. 8 is an enlarged and isolated perspective view of the injector adaptor 746, in accordance with an embodiment of the present invention.

The injector adaptor 746 includes a proximal portion 750 and a distal portion 752. In an embodiment, a ring 754 can be defined at the distal portion 752 sized to hold the barrel 748 of the syringe 742. In an embodiment, a receiving portion 756 can be provided at the proximal portion 750 configured to receive and mate to the plunger 744. In an embodiment, the plunger 744 of the syringe 742 can be snapped in at the receiving portion 756 so as to tightly hold the syringe 744 within the injector adaptor 746.

Referring to FIGS. 7 and 8, upon depression of the plunger 744, fluid flows from the syringe 742 through the luer hub 736, out through the handle 728, and into the hollow needle 724 and further into the patient's body. In an embodiment, the syringe 742, the plunger 744 and the injector adaptor 746 can be assembled by the operator.

In an embodiment, the injector adaptor 746 allows the operator to aspirate and inject the syringe 742 with the palm of the hand while the thumb and index finger is about the handle 728. The thumb and index finger can be used to push and steer the needle 724 via the handle 728.

In an embodiment, the operator also has the option of not using the syringe 742 or injector adaptor 746 and can place the needle via just the handle 728.

Figure 9:
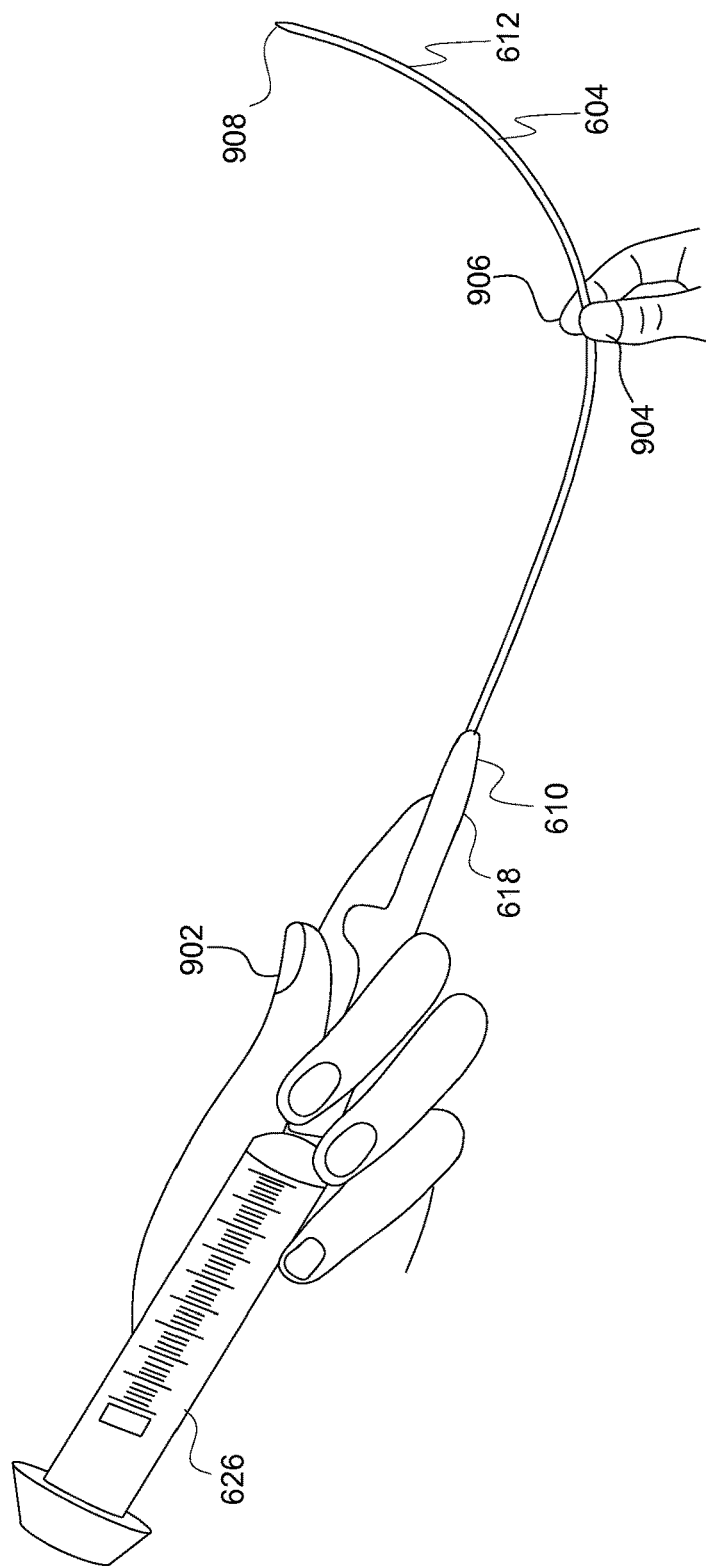
FIG. 9 illustrates handling the medical assembly of FIG. 6 for delivery in a patient's body, in accordance with an embodiment of the present invention.

FIG. 9 illustrates handling of the medical assembly 600 for delivery in a patient's body, in accordance with an embodiment of the present invention. Referring to the medical assembly 600, in an embodiment, as shown in FIG. 9, a physician or an operator can use the injector 626 as an extension of the handle 618 and grasp the handle 618 by using his thumb 902 (left hand) in a manner that the operator can hold the delivery device 610 completely. In some embodiments, the handle includes a substantially flat portion configured to facilitate in visual and tactile feedback during positioning and placement of the delivery device 610 within the body. In some embodiments, the handle 618 may have a bottom flat surface configured to indicate the orientation of a needle tip 908 by tactile and visual feedback to the operator. The substantially flat surface on the bottom surface is preferably sized and shaped to exploit forces applied to the handle 618 by the operator and provides a sufficiently firm surface upon which force may be applied to complete the operation. The actual grasping of the handle 618 by an operator is dictated by a variety of factors such as operator training, comfort, dexterity, strength, etc. In an embodiment, the operator can use his second hand (right hand) to grasp the first dilator 604, as shown in FIG. 9, with the use of the thumb 904 and the index finger 906 (right hand), to aid in directing including advancing and withdrawing the needle 612 of the delivery device 610 after the first dilator 604 has been locked to the handle 618. In an embodiment, the second hand or the finger of the second hand can be used to support the needle 612 such that the needle 612 can be inserted into the body opening along the passageway without any deflection because of the support provided by the finger to the needle 612, as shown in FIG. 9.

Figure 10:
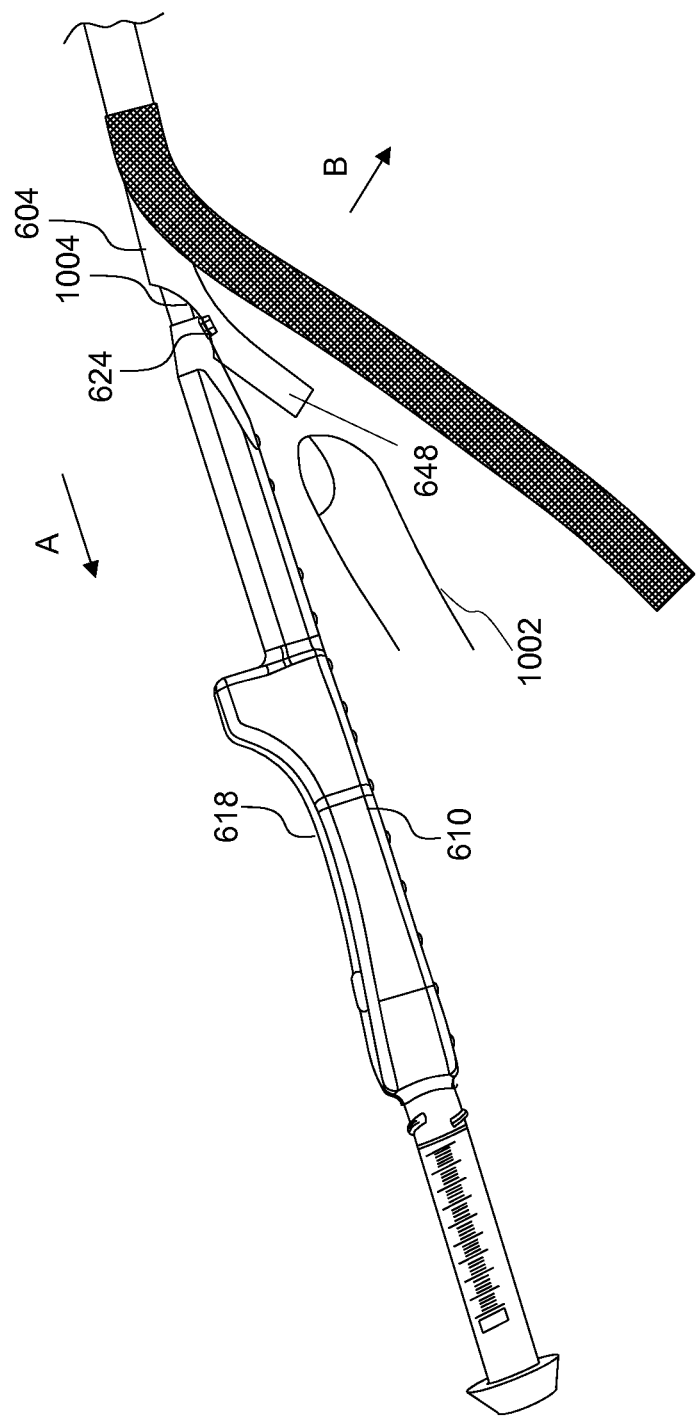
FIG. 10 illustrates handling the medical assembly of FIG. 6 for delivery in a patient's body, in accordance with an embodiment of the present invention.

FIG. 10 illustrates handling of the medical assembly 600 for delivery in a patient's body, in accordance with an embodiment of the present invention. Referring to the medical assembly 600, in an embodiment, as shown in FIG. 10, when the first dilator 604 is secured to the handle 618 by aligning the aperture 634 over the protrusion 624, the operator can additionally grasp the dilator 604 to manipulate the delivery device 610 into, about and through the patient. The operator can use his index finger to provide support to the needle 612 thereby directing the needle at a trajectory path towards its target location. In another embodiment, when the first dilator 604 and the needle 612 (not shown) are inserted through the patient, the operator can manipulate the delivery device 610 such as to disassociate the first dilator 604 from the delivery device 310. In such embodiments, as shown in FIG. 10, the operator can use his index finger 1002 to abut to the dilator tab 648 while the delivery device 810 is removed in the direction of an arrow A causing the dilator tab 648 and an edge 1004 of the aperture 634 to deflect in a direction of an arrow B, allowing the protrusion 624 to exit the aperture 634.

In some embodiments, another coupling mechanism or system may be used to couple the dilator 604 to the delivery device 610. For example, in some embodiments, the dilator 604 may be snap fit or frictionally fit to the delivery device 610. In some embodiments, the delivery device 610 includes or defines a cavity configured to receive a portion of the dilator to couple the dilator to the delivery device.

Figure 11A:
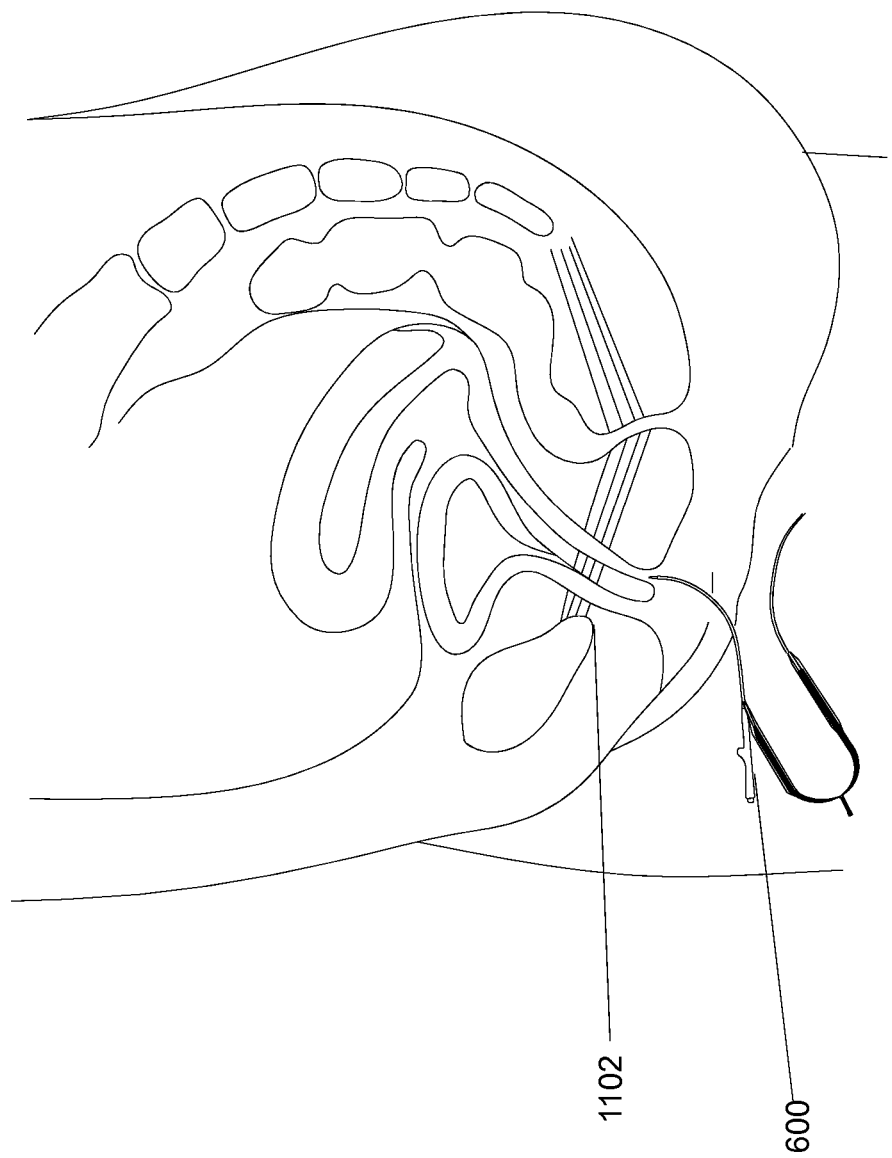
FIG. 11A illustrates positioning of a medical assembly for placement of an implant in a patient's body opening, in accordance with an embodiment of the present invention.

FIG. 11A illustrates positioning of the medical assembly 600 inside a female body through a vaginal approach. The method of positioning the medical assembly 1100 includes creating a vaginal incision in the vaginal space 1102.

Figure 11B:
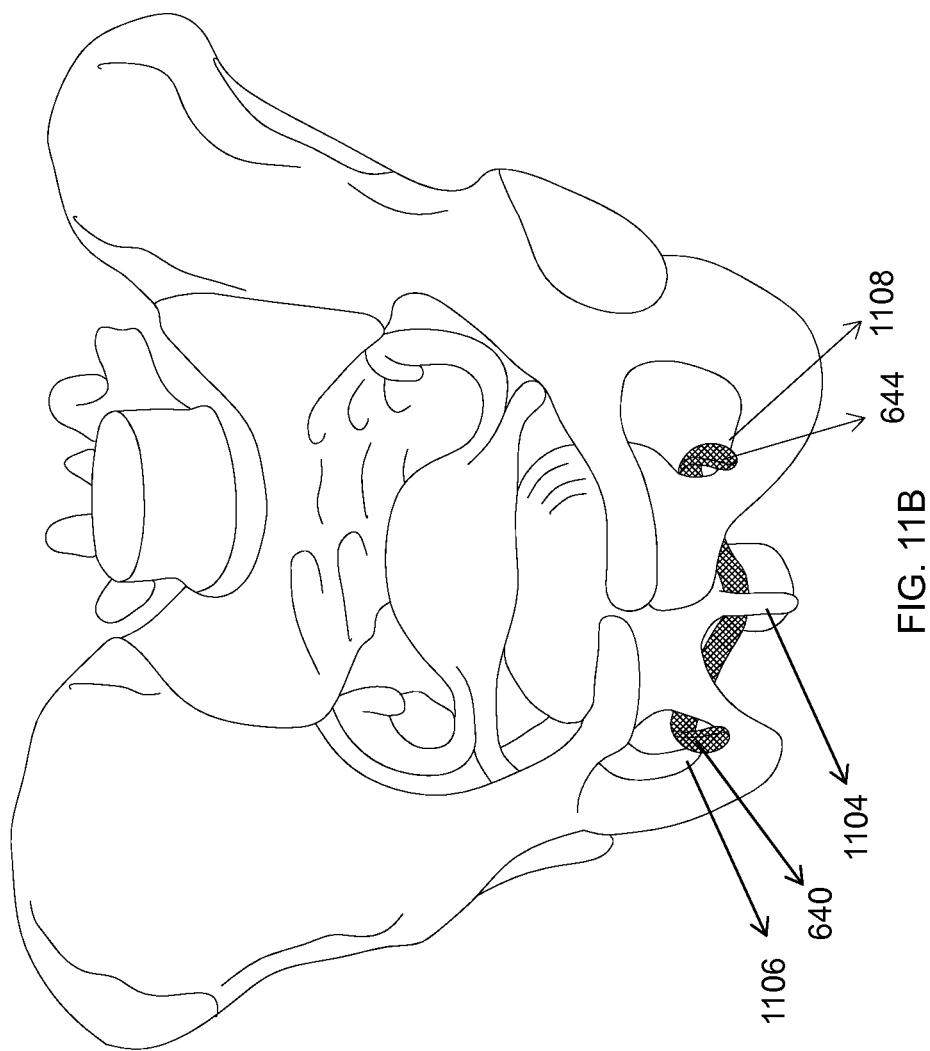
FIG. 11B illustrates implantation of a portion of the medical assembly inside a female body through a through a transobturator approach.

FIG. 11B illustrates implantation of the implant 602 inside a female body through a transobturator approach. In accordance with this approach, the implant 602 is passed under the urethra 1104 and out through incisions in a groin compartment of the thigh (not shown in the diagram). The first end portion 640 of the implant 602 can be attached at the first portion 1106 within the pelvic floor region. The second end portion 644 of the implant 602 can be attached at the second portion 1108 within the pelvic floor region. In an embodiment, the first end portion 1106 and the second end portion 1108 can be the obturator foreman tissues proximate the obturator foreman.

FIG. 11C illustrates implantation of the implant 602 inside the female body through a retropubic approach. The retropubic approach positions the implant 602 under the urethra 1104 in a U shape. The first end portion 640 and the second end portion 644 of the implant 602 are brought up behind a pubic bone 1110 and out through skin incisions above the pubic bone 1110, and coupled to tissues adjacent to the pubic bone 1110.

Figure 12:
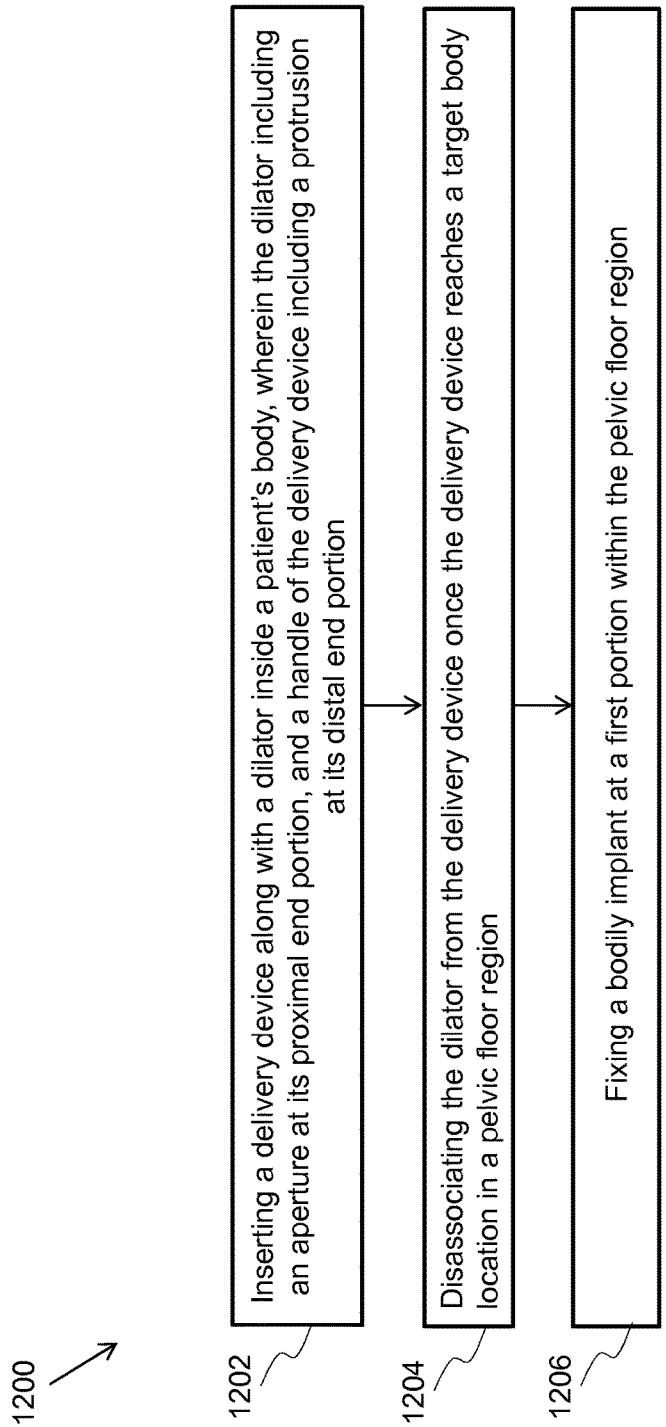
FIG. 12 illustrates a flowchart representing a method for delivery of a medical assembly in a patient's body, in accordance with an embodiment of the present invention.

FIG. 12 illustrates a flowchart representing a method 1200 for delivery of a medical assembly such as the medical assembly 600 or 700 in a patient's body for treatment of a pelvic floor disorder, in accordance with an embodiment of the present invention. In an embodiment, the pelvic floor region can be a retropubic region. Referring to FIG. 12, in conjunction with FIG. 6, the method of delivery and placement of the bodily implant 602 with the use of the medical assembly 600 is described in accordance with an embodiment of the present invention. The medical assembly 600 is hereafter used to describe the method in an exemplary embodiment. However, it must be appreciated that other medical assemblies such as the medical assembly 100 or 200 may also be employed in a similar manner. The medical assembly 100, medical assembly 200, and the medical assembly 600 have already been described in conjunction with various figures above.

The method 1200 includes inserting the delivery device 610 along with the dilator 604 inside the patient's body at step 1202. In an embodiment, the method 1200 may include creating a vaginal incision for delivery of the delivery device 610 and the dilator 604 within the body through a transvaginal approach. The dilator 604 including the aperture 634 at its proximal end portion 606 and the handle 618 of the delivery device 610 including the protrusion 624 at its distal end portion 622 can be aligned in a manner that the protrusion 624 is sized to fit in the aperture 634, thereby preventing the axial movement of the first dilator 604 with respect to the delivery device 610. In an embodiment, the method can include assembling the first dilator 604 and the delivery device 610 before the delivery into the patient's body such that the assembling includes sliding the protrusion 624 into the aperture 634 sized to frictionally retain the protrusion 624 and lock the first dilator 604 with the delivery device 610. The lock secures the first dilator 604 to the delivery device 610 allowing the operator to control and direct the needle 612 by means of the first dilator 304 positioned over the needle 612. In an embodiment, the medical assembly 600 can be pre-assembled and the operator may not be required to perform the step of assembling.

Once the first dilator 604 is secured to the handle 318 by alignment of the protrusion 624 onto the aperture 634, the operator can additionally grasp the dilator 604 to manipulate the delivery device 610 into, about and through the patient. Once the first dilator 604 and the needle 612 are inserted through the patient, the method includes positioning of the implant 602 at the target location of the pelvic floor region. Upon reaching of the implant 602 at its target location, the operator then tensions the implant 602 by pulling up the first dilator 604 and the first sleeve 636. The method further includes disassociating the first dilator 604 from the delivery device 610 once the delivery device 610 reaches the target location in a pelvic floor region by moving the first dilator 604 against the protrusion 624 and allowing the protrusion 624 to exit the aperture 634, at step 1204. In an embodiment, the disassociation of the first dilator 604 from the delivery device 610 can be done in a manner described in FIG. 10. For example, in some embodiments, the operator can use his finger to abut to the first dilator 604 while the delivery device 610 is removed causing the first dilator 604 and an edge 1004 of the aperture 634 to deflect thereby allowing the protrusion 624 to exit the aperture 634. In an embodiment, the disassociating can include deflecting the dilator tab 256 so as to slide or exit the protrusion from the aperture and unlock the dilator 604 from the delivery device 610. In an embodiment, the disassociation of the first dilator 604 from the delivery device 610 can be performed before tensioning the implant 602 while in another embodiment the disassociation can be performed after tensioning the implant 602.

In an embodiment, another delivery device similar to the delivery device 610 can be coupled to the second dilator 642 in a manner similar to that described above. In another embodiment, the delivery device 610 can be coupled to the second dilator 642 to implant the second end portion 644 to the target tissue location.

The method further includes removing the first dilator 604 from the patient's body after disassociating the first dilator 604 from the delivery device 610 once the delivery device 610 reaches the target body location in the pelvic floor region 906. The operator also disassociates the first sleeve 636 by cutting a suture, wherein the suture couples the first sleeve 636 with the first dilator 604 and the center tab 638 from the implant 602. In an embodiment, the first dilator 604 and the first sleeve 636 can be removed from the implant 602. The first sleeve 636 and the first dilator 604 can then be pulled out from the patient's body through incisions such as provided in an abdomen or in a groin or an obturator area of the patient. The second dilator 642 can also be removed in a similar manner. In some embodiments, separate sutures may be used to couple the sleeves and the center tab to the implant.

Upon implanting the implant 602 at the target location, at step 1206, the method further includes fixing the bodily implant at a first portion 606 within the pelvic floor region. In an embodiment, the pelvic floor region is a retropubic region. The method further comprises attaching the first end portion 640 and the second end portion 644 of the implant 602, respectively, at the first portion 1106 and the second portion 608 within the pelvic floor region 1106 as described in FIG. 11B.

The method includes removing the delivery device 610 from the patient's body after fixing the implant 602 or before tensioning or fixing the implant 602.

In accordance with some embodiments, the medical assembly 600 includes the injector 626 such as shown and described in conjunction with FIG. 6. In such embodiments, the method 1200 may include delivering medication such as anesthetics, medications, other fluids to assist in the healing process, or any other fluids to a target tissue in the patient's body with the use of the injector 626. In some embodiments, the injector 626 can be a syringe having an associated plunger such as the plunger 632 shown in FIG. 6. The method 1200 may include depressing the plunger 632 to cause the medication flow from the syringe 626 and into the patient's body. In an embodiment, when the dilator 604 is locked onto the handle 618, the operator can hold the dilator 604 with his one hand and press the plunger 632 to aspirate and inject the medication with the other hand during insertion of the medical assembly 600 inside the body. In an embodiment, the medication is injected directly into a needle track where an implant such as the implant 602 is eventually positioned to help with post-operative pain.

In some embodiments, the medial assembly as described above, may be used in portions or locations within the body other than the pelvic region of the patient. For example, the medial assembly may be used to insert and implant and provide support to any portion of a body of a patient.

In some embodiments, a medical assembly includes a sling assembly including a dilator and an implant, the dilator configured to be coupled to the implant and including a proximal portion and a distal portion, wherein the proximal portion includes a first locking feature, wherein the dilator includes a dilator tab extending proximally to the dilator and configured to allow movement of the dilator with respect to the tab; a delivery device configured to deliver the sling assembly and including a needle having a proximal portion and a distal portion such that the dilator is positioned over the needle; and a handle having a proximal portion and a distal portion, wherein the distal portion of the handle is coupled to the proximal portion of the needle, the distal portion of the handle including a second locking feature configured to releasably mate with the first locking feature, the first locking feature sized to frictionally retain the second locking feature at one location.

In some embodiments, the first locking feature is an aperture. In some embodiments, the second locking feature is a protrusion. In some embodiments, the sling assembly includes a retropubic incontinence sling configured to be delivered by way of a transvaginal approach or a transobturator approach or a vaginal pre-pubic approach. In some embodiments, the needle is a surgical needle with a substantially small outer diameter for minimally invasive surgery. In some embodiments, the surgical needle includes a through lumen such that when coupled to the handle, an entire length of the handle and the needle defines a passageway.

In some embodiments, the assembly includes an injector configured to be coupled to the proximal portion of the handle and configured to deliver a fluid through the passageway to a location inside the body.

In some embodiments, the handle includes a substantially flat portion configured to facilitate in visual and tactile feedback during positioning and placement of the delivery device within the body. In some embodiments, the dilator tab is configured to facilitate in disassociation of the dilator from the delivery device. In some embodiments, the dilator tab is defined by a flattened proximal portion of the dilator. In some embodiments, the dilator tab is defined as a close ended and rounded portion extending at the proximal end of the dilator.

In some embodiments, a medical assembly includes an implant for placement in a body of a patient; a dilator configured to be coupled to the implant and including a proximal portion and a distal portion, the proximal portion including an aperture wherein the dilator includes a dilator tab extending proximally to the dilator and configured to allow movement of the dilator with respect to the tab; a delivery device configured to deliver the implant and including a hollow needle having a proximal portion and a distal portion such that the dilator is positioned over the hollow needle; and a handle having a proximal portion and a distal portion, wherein the distal portion of the handle is coupled to the proximal portion of the needle, the distal portion of the handle including a protrusion configured to releasably fit into the aperture and inhibiting axial movement of the dilator with respect to the delivery device, the aperture sized to frictionally retain the protrusion of the delivery device; and an injector configured to be coupled to the proximal end portion of the handle.

In some embodiments, the handle includes a through lumen such that when coupled to the needle, an entire length of the handle and the needle defines a passageway to inject fluid in the patient's body.

In some embodiments, the medical assembly includes at least one injector port having a through lumen and configured to connect the injector with the handle. In some embodiments, the injector includes at least one of a syringe, plunger, pump, nozzle, and a valve.

In some embodiments, a method for treatment of a pelvic floor disorder in a patient's body, the method includes inserting a delivery device along with a dilator inside the patient's body, wherein the dilator includes an aperture at its proximal end portion and a dilator tab extending proximally to the dilator, the delivery device including a handle with a protrusion at its distal end portion such that the protrusion is sized to fit in the aperture thereby preventing an axial movement of the dilator with respect to the delivery device; disassociating the dilator from the delivery device once the delivery device reaches a target body location in a pelvic floor region by moving the dilator against the protrusion and allowing the protrusion to exit the aperture; and fixing a bodily implant at a first portion within the pelvic floor region.

In some embodiments, the method includes assembling the dilator and the delivery device before delivery into the patient's body, wherein the assembling includes sliding the protrusion into the aperture sized to frictionally retain the protrusion and lock the dilator with the delivery device. In some embodiments, the method includes creating a vaginal incision for delivery of the delivery device and the dilator within the body through a trans-vaginal approach. In some embodiments, the pelvic floor region is a retropubic region.

In some embodiments, the method includes removing the dilator from the patient's body after disassociating the dilator from the delivery device once the delivery device reaches the target body location in the pelvic floor region.

In some embodiments, the dilator is coupled to the implant and the method includes attaching a first end portion of the implant at the first portion within the pelvic floor region. In some embodiments, the method includes attaching a second end portion of the implant at a second portion within the pelvic floor region. In some embodiments, the method includes removing the delivery device from the patient's body after fixing the implant. In some embodiments, the disassociating further includes deflecting the dilator tab so as to exit the protrusion from the aperture and unlock the dilator from the delivery device. In some embodiments, the delivery device is coupled to an injector and the method includes delivering medication to a target tissue in the body of the patient with the use of the injector.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the disclosure.

What is claimed is:

1. A medical assembly comprising:
  a sling assembly including a dilator and an implant, the dilator configured to be coupled to the implant and including a proximal portion and a distal portion, the proximal portion including a first locking feature, the first locking feature including an aperture, the dilator including a dilator tab flexibly coupled to the proximal portion of the dilator, the aperture being disposed on the dilator at a location distal to the dilator tab, the dilator having a first opening, a second opening, and a lumen extending from the first opening to the second opening;
  a delivery device configured to deliver the sling assembly and comprising:
    a needle having a proximal portion and a distal portion, the needle being inserted through the first opening of the dilator such that a portion of the needle is disposed within the lumen of the dilator and a needle tip of the needle distally extends from the second opening of the dilator; and
    a handle having a proximal portion and a distal portion, the distal portion of the handle being coupled to the proximal portion of the needle, the distal portion of the handle fixably extending from the proximal portion of the handle, the distal portion of the handle including a second locking feature configured to releasably couple to the first locking feature, the second locking feature including a protrusion, the protrusion being linear, the first locking feature being sized to frictionally retain the second locking feature at one location,
  the second locking feature configured to be uncoupled from the first locking feature, the dilator tab flexing away from the proximal portion of the dilator to uncouple the protrusion from the aperture in response to user pressure applied directly to the dilator tab.

2. The medical assembly of claim 1, wherein the implant includes a retropubic incontinence sling configured to be delivered by way of a transvaginal approach or a transobturator approach or a vaginal pre-pubic approach.

3. The medical assembly of claim 1, wherein the needle defines grooves along an outer surface of the needle.

4. The medical assembly of claim 1, wherein the needle includes a through lumen such that when coupled to the handle, an entire length of the handle and the needle defines a passageway.

5. The medical assembly of claim 4, further comprising:
  an injector configured to be coupled to the proximal portion of the handle and configured to deliver a fluid through the passageway to a location inside a body of a patient.

6. The medical assembly of claim 1, wherein the handle includes a substantially flat portion configured to facilitate in visual and tactile feedback during positioning and placement of the delivery device within a body of a patient.

7. The medical assembly of claim 1, wherein the dilator tab is defined by a flattened portion that extends from the proximal portion of the dilator at a non-zero angle.

8. The medical assembly of claim 1, wherein the dilator tab includes a close ended and rounded portion extending from the proximal portion of the dilator.

9. The medical assembly of claim 1, further comprising a syringe having a plunger, the syringe configured to be coupled to the proximal portion of the handle, wherein, upon depression of the plunger, fluid flows from the syringe through the handle and the needle, and out of a distal end of the needle.

10. The medical assembly of claim 1, wherein the dilator is a first dilator, wherein the sling assembly further includes a second dilator, and a tab, the implant having an first end portion and a second end portion, the first dilator coupled to the first end portion of the implant, the second dilator coupled to the second end portion of the implant, the tab being coupled to a portion of the implant between the first end portion and the second end portion.

11. A medical assembly comprising:
  an implant for placement in a body of a patient, the implant having a first end portion and a second end portion;
  a first dilator configured to be coupled to the first end portion of the implant and including a proximal portion and a distal portion, the proximal portion including an aperture, the first dilator including a dilator tab flexible coupled to the proximal portion of the first dilator, the aperture being disposed on the first dilator at a location distal to the dilator tab, the first dilator has a first opening, a second opening, and a lumen extending from the first opening to the second opening;
  a second dilator configured to the second end portion of the implant;
  a tab coupled to a portion of the implant between the first end portion and the second end portion; and
  a delivery device configured to deliver the implant and comprising:
    a hollow needle having a proximal portion and a distal portion, the first dilator being positioned over the hollow needle, the hollow needle being inserted through the first opening of the first dilator such that a portion of the hollow needle is disposed within the lumen of the first dilator and a needle tip of the hollow needle distally extends from the second opening of the first dilator; and
    a handle having a proximal portion and a distal portion, the distal portion of the handle being coupled to the proximal portion of the hollow needle, the distal portion of the handle including a linear protrusion configured to releasably fit into the aperture, the aperture sized to frictionally retain the protrusion of the delivery device, the proximal portion of the handle including an injection portion; and
  a syringe having a plunger, the syringe configured to be coupled to the injector port.

12. The medical assembly of claim 11, wherein the handle includes a through lumen such that when coupled to the hollow needle, an entire length of the handle and the hollow needle defines a passageway to inject fluid in the body of the patient.

* * * * *